United States Patent
Naito (10) Patent No.: US 11,478,562 B2
(45) Date of Patent: Oct. 25, 2022

(54) METHOD OF MAINTAINING STERILE ENVIRONMENT OF WORKING CHAMBER, AND STERILE ENVIRONMENT MAINTAINING APPARATUS

(71) Applicant: Ushio Denki Kabushiki Kaisha, Tokyo (JP)

(72) Inventor: Keisuke Naito, Tokyo (JP)

(73) Assignee: Ushio Denki Kabushiki Kaisha, Tokyo (JP)

( * ) Notice: Subject to any disclaimer, the term of this patent is extended or adjusted under 35 U.S.C. 154(b) by 19 days.

(21) Appl. No.: 15/930,283

(22) Filed: May 12, 2020

(65) Prior Publication Data
US 2020/0360551 A1 Nov. 19, 2020

(30) Foreign Application Priority Data
May 13, 2019 (JP) .............................. JP2019-090797

(51) Int. Cl.
*A61L 2/20* (2006.01)
*A61L 2/04* (2006.01)
(Continued)

(52) U.S. Cl.
CPC ................. *A61L 2/202* (2013.01); *A61L 2/04* (2013.01); *A61L 2/084* (2013.01); *A61L 2/085* (2013.01);
(Continued)

(58) Field of Classification Search
CPC . A61L 2/202; A61L 2/04; A61L 2/084; A61L 2/085; A61L 2/10; A61L 2/208; A61L 2/022
See application file for complete search history.

(56) References Cited

U.S. PATENT DOCUMENTS

| | | | | |
|---|---|---|---|---|
| 4,427,636 A | * | 1/1984 | Obenshain | B01J 19/122 204/157.5 |
| 7,344,685 B2 | * | 3/2008 | McNulty | A61L 2/202 422/186.07 |
| 2010/0112677 A1 | | 5/2010 | Onishi et al. | |

FOREIGN PATENT DOCUMENTS

JP 5484681 B2 5/2014

OTHER PUBLICATIONS

Orphal, J. "A critical review of the absorption cross-sections of O3 and NO2 in the ultraviolet and visible." Journal of Photochemistry and Photobiology A: Chemistry 157 (2003) 185-209. (Year: 2003).*

(Continued)

*Primary Examiner* — Timothy C Cleveland
(74) *Attorney, Agent, or Firm* — Studebaker & Brackett PC (57) ABSTRACT

A technique is provided whereby hydrogen peroxide introduced into a working chamber containing a resin component is reduced to a low concentration in a shorter time than before. The present invention resides in a method of maintaining a sterile environment of a working chamber that contains a resin component, and includes a step (a) of introducing hydrogen peroxide into the working chamber, a step (b) of introducing air into the working chamber through a filter after completion of the step (a), a step (c) of generating ozone by irradiating the air with ultraviolet having a peak wavelength of from 160 nm to less than 200 nm upstream of the filter or inside the working chamber and introducing the ozone into the working chamber, and a step (d) of decomposing the ozone introduced into the working chamber into oxygen radicals.

9 Claims, 9 Drawing Sheets

(51) Int. Cl.
*A61L 2/08* (2006.01)
*A61L 2/10* (2006.01)
*A61L 2/02* (2006.01)

(52) U.S. Cl.
CPC ............... *A61L 2/10* (2013.01); *A61L 2/208* (2013.01); *A61L 2/022* (2013.01)

(56) References Cited

OTHER PUBLICATIONS

The extended European search report issued by the European Patent Office dated Jan. 12, 2021, which corresponds to European Patent Applicatio No. 20173986.9-1104 and is related to U.S. Appl. No. 15/930,283.

* cited by examiner

METHOD OF MAINTAINING STERILE ENVIRONMENT OF WORKING CHAMBER, AND STERILE ENVIRONMENT MAINTAINING APPARATUS

BACKGROUND OF THE INVENTION

Field of the Invention

The present invention relates to a method of maintaining a sterile environment of a working chamber, and to a sterile environment maintaining apparatus.

Description of the Related Art

In production of products that require a high degree of quality control such as pharmaceuticals, the products and containers are not only sterilized, but also various steps such as packaging and closure are performed inside a sealed sterile environment maintaining apparatus such as an isolator. A sterile environment maintaining apparatus is used not only for producing such products but also when it is required to absolutely prevent substances other than those necessary for the work from mixing into the working chamber, such as culturing cells.

In order to maintain a sterile environment, air is taken into a working chamber of the sterile environment maintaining apparatus from outside the working chamber via a particle trapping air filter such as a HEPA (High Efficiency Particulate Air) filter.

When an operation inside the working chamber is complete, the existing sterile environment maintaining apparatus introduces hydrogen peroxide into the working chamber to sterilize the interior of the working chamber before proceeding to a next operation. After that, process steps of exhausting and removing the hydrogen peroxide introduced into the working chamber are carried out by supplying air into the working chamber (also referred to as "aeration").

One issue here is that it takes a long time for this aeration process to reduce the concentration of the hydrogen peroxide present in the working chamber to or below a predetermined reference value. Currently, ACGIH (American Conference of Governmental Hygienists), for example, specifies that hydrogen peroxide should be at or below 1 ppm as a safety standard, and the Ministry of Health, Labor, and Welfare of Japan recommends this value, too. While it depends on the size of the working chamber, an aeration process for a long period of 5 or 6 hours may be required in some cases in order to reduce the level of hydrogen peroxide inside the working chamber at or below 1 ppm by introducing clean air.

Patent Document 1 listed below points out that the hydrogen peroxide adhered to the HEPA filter is the cause of the long hours it takes to reduce the concentration of the hydrogen peroxide in the working chamber. According to Patent Document 1, the aeration process alone, in which clean air is simply introduced into the working chamber, cannot remove the hydrogen peroxide adhered to the HEPA filter in a short time. The document discloses a method of spraying ozone supplied from an ozone supply, tube to the HEPA filter, and a method of irradiating both surfaces of the HEPA filter with ultraviolet from an ultraviolet lamp, for the purpose of decomposing the hydrogen peroxide adhered to the HEPA filter.

PRIOR ART DOCUMENT

Patent Document

Patent Document 1: Japanese Patent No. 5484681

SUMMARY OF THE INVENTION

The methods described in Patent Document 1 listed above are assumed to be effective in decomposing the hydrogen peroxide adhered to the HEPA filter in a short time after the hydrogen peroxide that existed in the working chamber has been exhausted sufficiently by aeration. However, in the case where hydrogen peroxide still remains in the working chamber, the methods described in Patent Document 1 are not a fundamental solution for decomposing the hydrogen peroxide in a short time.

A working chamber of a sterile environment maintaining apparatus such as an isolator often contains resin components made of fluoride rubber, silicone, vinyl chloride, polyethylene, and so on in addition to metal components made of stainless steel or aluminum. For example, some rollers used for conveying a container filled with a pharmaceutical agent as an object on which work is to be performed inside the working chamber from an upstream side to a downstream side are composed of resin components. Namely, it is common that the placement unit (placement table) on which the object being worked on is placed inside the working chamber is composed of resin components.

Hydrogen peroxide is expected to adsorb to and penetrate into these resin components equipped inside the working chamber. When this is the case, while the hydrogen peroxide present in the working chamber is exhausted out of the working chamber by letting clean air flow into the working chamber, the hydrogen peroxide that has penetrated into the resin components gradually moves toward the surface as it vaporizes, and is released into the working chamber. Because of this, it is not possible to reduce the concentration of hydrogen peroxide to a desired value within a short period of time.

A method of introducing ozone supplied from an ozone supply tube into the working chamber is conceivable in view of the method described in Patent Document 1. Patent Document 1 suggests a method of using ozone mist generated by electrical decomposition, and a method of using ozone gas generated by an electrical discharge to oxygen supplied to an electrical discharge ozone generator.

However, introducing ozone mist into the working chamber makes the surfaces of resin components present inside the working chamber very wet, which requires an additional step such as wiping and drying processes. Introducing ozone created by an electrical discharge ozone generator into the working chamber leads to creation of nitric acid resulting from the reaction between $NO_X$ generated during the electrical discharge and the water, and the nitric acid may corrode metal components present inside the working chamber. Patent Document 1 specifically uses wet ozone that is passed through water after the electrical discharge. If such wet ozone is introduced into the working chamber, it is highly likely that nitric acid may also be introduced into the working chamber with the wet ozone.

As mentioned above, Patent Document 1 also discloses a method of decomposing hydrogen peroxide adhered to the HEPA filter by irradiating both surfaces of the HEPA filter with ultraviolet. This method is considered to be effective in a case where the object carrying the hydrogen peroxide to be decomposed is a component in a planar shape that is present at a specific location, such as the HEPA filter, and where a light source can be disposed reasonably close to the object. To decompose hydrogen peroxide remaining inside the working chamber by ultraviolet radiation, however, it would be necessary to dispose a large number of ultraviolet lamps inside the working chamber, which may be difficult in the first place because of the nature of the sterile environment maintaining apparatus. Moreover, direct irradiation of resin components with ultraviolet at a luminance desirable when ultraviolet radiation is used for decomposition of hydrogen peroxide may lead to degradation of these components.

Depending on the contents of operation performed to the object inside the working chamber, hydrogen peroxide, even at a concentration of 1 ppm or lower, may affect the object. In such a case, the aeration step in existing methods is expected to take even more time to reduce the concentration of hydrogen peroxide to or below a reference value. Accordingly, a technique that allows for reduction of the concentration of hydrogen peroxide inside a working chamber in a shorter time is desirable.

In view of the problems described above, an object of the present invention is to provide a technique whereby hydrogen peroxide introduced into a working chamber containing resin components is reduced to a low concentration in a shorter time than before. Another object of the present invention is to provide a sterile environment maintaining apparatus that allows hydrogen peroxide, which has been introduced to generate a sterile environment, to be reduced to a low concentration in a shorter time than before.

The present invention resides in a method of maintaining a sterile environment of a working chamber that contains a resin component, including:

a step (a) of introducing hydrogen peroxide into the working chamber;

a step (b) of introducing air into the working chamber through a filter after completion of the step (a);

a step (c) of generating ozone by irradiating the air with ultraviolet having a peak wavelength of from 160 nm to less than 200 nm upstream of the filter or inside the working chamber and introducing the ozone into the working chamber; and a step (d) of decomposing the ozone introduced into the working chamber into oxygen radicals.

Step (c) includes a step of generating ozone by irradiating the air with ultraviolet having a peak wavelength of from 160 nm to less than 200 nm. The light energy of the ultraviolet used in this step (c) is higher than e bond energy of the oxygen molecules that exist in the air, and lower than the bond energy of the nitrogen molecules. Therefore, step (c) does not cause generation of nitrogen radicals. Thus nitric acid, which results from a reaction with water that may be contained in the air, is not generated. Accordingly, there is no possibility of the equipment inside the working chamber (in particular, metal components) being corroded.

The ultraviolet emitted in step (c) is used for generating ozone not for decomposing hydrogen peroxide. Therefore, there is no need to entirely irradiate the inside of the working chamber with a high amount of ultraviolet.

The ozone readily spreads inside the working chamber with air currents, and can easily contact the hydrogen peroxide remaining in the working chamber. The method according to the present invention includes step (d) of decomposing ozone into oxygen radicals, rather than simply causing the ozone to react with the hydrogen peroxide. As the oxygen radicals that are more reactive act on the hydrogen peroxide, the hydrogen peroxide can be decomposed faster than before.

The ozone introduced by step (C), in particular, readily spreads and adheres also to the surfaces of resin components inside the working chamber. When the ozone is decomposed into more reactive oxygen radicals by step (d), the oxygen radicals react with hydrogen peroxide and turn to water ($H_2O$). The reaction with the hydrogen peroxide occurring on the surfaces of resin components causes a reduction in the concentration of the hydrogen peroxide on the surfaces of the resin components. This consequently creates a gradient in the concentration of hydrogen peroxide between the surface and the inside of the resin components, and the concentration difference causes the hydrogen peroxide that has penetrated into the resin components to vaporize and move toward the surface. This way, the decomposition reaction of hydrogen peroxide occurs successively.

According to the method described above, even the hydrogen peroxide that has penetrated into the resin components is decomposed in a short time, so that the residual concentration of hydrogen peroxide inside the working chamber can be reduced faster than before. Moreover, since ozone that is generated free of $NO_X$ is used, there is no possibility that the equipment inside the working chamber (in particular, metal equipment) is corroded.

Step (c) may be started later than the start of step (b).

According to the method described above, the ozone is introduced into the working chamber after the hydrogen peroxide has been exhausted from the working chamber to some extent. Since the concentration of hydrogen peroxide has been reduced to some extent at the time when oxygen radicals obtained by step (d) are introduced into the working chamber, the time required for reducing the hydrogen peroxide concentration to a desired value is shortened.

In the method of maintaining a sterile environment of a working chamber, step (c) may include a time period in which introduction of the air into the working chamber is stopped.

According to this method, there is a time period in which introduction of air into the working chamber is stopped when ozone is being introduced, so that the ozone concentration can be raised at a higher rate. This consequently increases the concentration of oxygen radicals in the working chamber obtained through step (d), so that the concentration of hydrogen peroxide inside the working chamber can be reduced at a higher rate.

Step (d) may adopt various methods.

For example, step (d) may include a step (d1) of emitting visible light of a wavelength of 450 nm to 800 nm into the working chamber. In this case, if there is provided a visible light source for illuminating the interior of the working chamber, the illumination light from this visible light source can be used as the visible light. To accelerate the decomposition at step (d), the visible light source may be controlled to raise the illuminance. If there is provided no such visible light source, the visible light may be emitted from outside the working chamber into the working chamber.

The ozone irradiated with the visible light is decomposed into oxygen radicals by the light energy originating from the visible light given to the ozone.

In another example, step (d) may include a step (d2) of emitting infrared light of a wavelength of 1500 nm to 3000 nm into the working chamber. The infrared light source that emits the infrared light may be disposed inside the working chamber, or outside the working chamber.

The ozone irradiated with the infrared light is decomposed into oxygen radicals by the heat energy originating from the infrared light given to the ozone. This infrared light radiated to the hydrogen peroxide raises the temperature of the hydrogen peroxide, and improves the reactivity. This allows the hydrogen peroxide that has penetrated into the resin components in the working chamber to readily diffuse to the surface, and raises the rate of decomposition of the hydrogen peroxide.

In another example, step (d) may include a step (d3) of emitting ultraviolet of a wavelength of 190 nm to 320 nm from a light source disposed inside the working chamber. Generally, wall surfaces of the working chamber are made of a glass material or the like, which may not transmit ultraviolet of this wavelength band. Therefore it is preferable to dispose the ultraviolet light source inside the working chamber if the ozone is to be decomposed using the ultraviolet of this wavelength band.

When this is the case, the ultraviolet light source used at step (d) may be the same one as the ultraviolet light source used at step (c).

Step (d1) may be a step of emitting flash light of the visible range. This enables instantaneous injection of high energy to the ozone, which generates oxygen radicals at a high concentration. Since oxygen radicals are extremely reactive and short-lived, the instantaneous generation of a large amount of oxygen radicals is effective also from the view point of increasing the decomposition efficiency of hydrogen peroxide.

Similarly, step (d2) may be a step of emitting flash light of the infrared range. Similarly, step (d3) may be a step of emitting flash light of the ultraviolet range.

In another example, step (d) may include a step (d4) of introducing water mist into the working chamber in parallel with step (c).

According to this method, the humidity inside the working chamber is increased, so that the ozone can more readily contact water molecules. The ozone is decomposed into oxygen and oxygen radicals by this contact with the water. Thus the concentration of oxygen radicals is increased.

In another example, step (d) may include a step (d5) of raising the temperature in the working chamber after execution of step (c).

According to this method, the temperature inside the working chamber is increased so that, as with the irradiation of ozone with infrared light, the ozone is more easily decomposed, and the concentration of oxygen radicals is increased.

Step (d) may include any one of the steps (d1) (d5) described above, or may include two or more of the steps (d1) to (d5).

A sterile environment maintaining apparatus according to the present invention includes:

a working chamber which contains a resin component disposed therein and in which a sterile environment is to be maintained;

an inlet port for allowing a gas to flow into the working chamber;

an exhaust port for allowing a gas to flow out of the working chamber;

a filter disposed upstream of the inlet port;

a hydrogen peroxide supply device supplying hydrogen peroxide into the working chamber;

a first ultraviolet light source disposed inside the working chamber or upstream of the inlet port and capable of emitting ultraviolet having a peak wavelength of from 160 nm to less than 200 nm; and an ozone decomposition means decomposing ozone present in the working chamber into oxygen radicals.

With the above sterile environment maintaining apparatus, the ozone that is generated by irradiating air with ultraviolet emitted from the first ultraviolet light source is introduced into the working chamber, after which the ozone present in the working chamber is decomposed by the ozone decomposition means at an accelerated reaction rate, so that the ozone is decomposed into oxygen radicals that are more reactive than the ozone. This way, a sterile environment maintaining apparatus capable of decomposing hydrogen peroxide remaining inside the working chamber after the completion of sterilization by hydrogen peroxide faster than before is realized.

The ozone decomposition means may include one or more selected from the group consisting of a visible light source emitting visible light of a wavelength of 450 nm to 800 nm in the working chamber, an infrared light source emitting infrared light of a wavelength of 1500 nm to 3000 nm in the working chamber, a second ultraviolet light source emitting ultraviolet of a wavelength of 190 nm to 320 nm in the working chamber, a humidifier device for humidifying the inside of the working chamber, and a heater device for raising the temperature in the working chamber.

According to the present invention, even when a working chamber contains resin components, hydrogen peroxide that was introduced into the working chamber for sterilization can be reduced to a low concentration in a shorter time than before.

DETAILED DESCRIPTION OF THE PREFERRED EMBODIMENTS

Embodiments of a sterile environment maintaining method and a sterile environment maintaining apparatus according to the present invention will be described below with reference to the applicable drawings. The drawings referred to below each present a schematic illustration and the dimensional ratios in the drawings are not necessarily the same as the actual dimensional ratios. The dimensional ratios in various figures of the drawings are not necessarily the same, either.

First Embodiment

Figure 1:
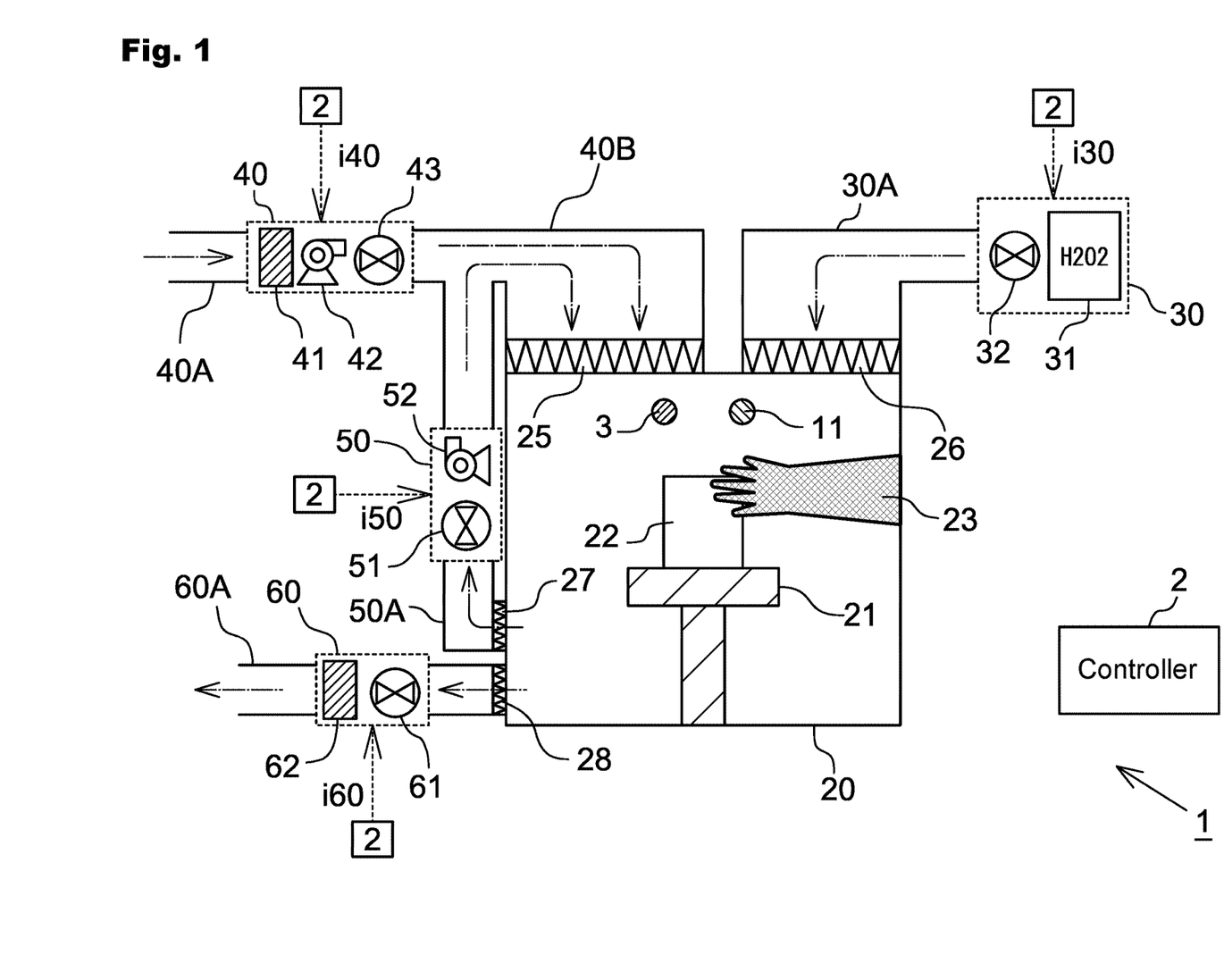
FIG. 1 is a drawing illustrating a schematic configuration of a sterile environment maintaining apparatus according to a first embodiment of the present invention.

FIG. 1 is a drawing illustrating a schematic configuration of a sterile environment maintaining apparatus according to a first embodiment of the present invention. The sterile environment maintaining apparatus 1 includes a working chamber 20 in which a sterile environment is to be maintained. The working chamber 20 is provided with gloves 23 isolated from inside of the working chamber 20. An operator can manipulate a work object 22 set on a placement unit 21 inside the working chamber 20 via the gloves 23 to carry out operations on the work object 22 with the sterile environment being maintained.

<<Confiauration>>

The work object 22 is, for example, a container for holding a pharmaceutical agent, or a plate for culturing cells, which requires operation in a sterile environment. The placement unit 21 serves the function as a pedestal on which the work object 22 is placed. The placement unit 21 includes a resin component made of a material such as fluorine rubber, silicone, vinyl chloride, polyethylene and the like, to prevent breakage or cracking of the work object 22.

There may be metal components provided in parts (not shown) inside the working chamber 20.

The sterile environment maintaining apparatus 1 illustrated in FIG. 1 is configured to be able to supply air into the working chamber 20 and to exhaust air form the working chamber 20. More particularly, the sterile environment maintaining apparatus 1 includes a hydrogen peroxide introduction system 30 for introducing hydrogen peroxide for sterilization into the working chamber 20, a clean air introduction system 40 for introducing clean air for aeration, a gas circulation system 50 for taking out a gas from the working chamber 20 and returning the gas into the working chamber 20, and an exhaust system 60 for exhausting a gas from the working chamber 20 to the outside.

The sterile environment maintaining apparatus 1 also includes a controller 2 for controlling the hydrogen peroxide introduction system 30, clean air introduction system 40, gas circulation system 50, and exhaust system 60. The controller 2 is a functional means that executes control of the overall operation of the sterile environment maintaining apparatus 1 and configured by dedicated hardware and/or software.

The hydrogen peroxide introduction system 30 includes a hydrogen peroxide gas source 31 and a valve 32. The degree of opening of the valve 32 is adjusted based on a control signal i30 from the controller 2. With the valve 32 being controlled, hydrogen peroxide gas is supplied from the hydrogen peroxide gas source 31 into the working chamber 20 through a pipe 30A. A HEPA filter 26 is provided in the pipe 30A for the purpose of trapping particles, and the hydrogen peroxide gas is supplied into the working chamber 20 through this HEPA filter 26.

The clean air introduction system 40 includes a catalyst 41, a blower 42, and a valve 43. The blower 42 and valve 43 are controlled based on a control signal i40 from the controller 2. The operation of the blower 42 and the degree of opening of the valve 43 are controlled by the controller 2 so that clean air taken in from an air inlet pipe 40A is supplied into the working chamber 20 through a pipe 40B. A HEPA filter 25 is provided in the pipe 40B for the purpose of trapping particles, and clean air is supplied into the working chamber 20 through this HEPA filter 25.

Namely, in this embodiment, the pipe 40B corresponds to an "inlet port" for introduction of clean air into the working chamber 20 through the HEPA filter 25.

The catalyst 41 is provided for the purpose of decomposing hydrogen peroxide or ozone in the event that the hydrogen peroxide or ozone present in the working chamber 20 are discharged to the space outside the working chamber 20 through the pipe 40A. The catalyst is made of manganese dioxide, for example. If there is no possibility of the gas present in the working chamber 20 being discharged out of the system through the pipe 40A, the apparatus may be configured without the catalyst 41.

The gas circulation system 50 includes a valve 51 and a blower 52. The valve 51 and blower 52 are controlled based on a control signal i50 from the controller 2. The valve 51 and blower 52 are controlled so that the gas that was staying in the working chamber 20 is taken out through a pipe 50A, circulated, and supplied again into the working chamber 20 via the pipe 40B. As illustrated in FIG. 1, the pipe 50A may also be provided with a HEPA filter 27.

If it is possible to circulate the gas through the pipe 50A only by adjustment of the degree of opening of the valve 51, the blower 52 need not necessarily be provided.

The exhaust system 60 includes a valve 61 and a catalyst 62. The degree of opening of the valve 61 is adjusted based on a control signal i60 from the controller 2. The catalyst 62 is a catalyst for decomposing hydrogen peroxide or ozone and made of a material similar to that of the catalyst 41 mentioned above. The valve 61 is controlled to open so that the gas that was staying in the working chamber 20 is passed through the catalyst 62, and exhausted to the outside of the working chamber 20, i.e., out of the system, through a pipe 60A. Even if hydrogen peroxide or ozone is present in the working chamber 20, the exhaust gas discharged out of the system contains a concentration of hydrogen peroxide or ozone reduced to or below the level specified by the safety standard, since the ozone adsorbs to and is decomposed by the catalyst 62.

Namely, in this embodiment, the pipe 60A corresponds to an "exhaust port" that allows the gas inside the working chamber 20 to be exhausted out of the sterile environment maintaining apparatus 1.

In this embodiment, the sterile environment maintaining apparatus 1 includes a first ultraviolet light source 3 and a visible light source 11 inside the working chamber 20. The first ultraviolet light source 3 is a light source capable of emitting ultraviolet having a peak wavelength of from 160 nm to less than 200 nm, and may be an excimer lamp containing a sealed-in light emitting gas including, for example, xenon (Xe). The visible light source 11 is a light source capable of emitting visible light of a wavelength of 450 nm to 800 nm, and may be a white LED, for example. The first ultraviolet light source 3 and visible light source 11 are configured to be illuminated by the controller 2.

<<Sterile Environment Maintaining Method>>

The process steps of sterilizing the interior of the working chamber 20 of the sterile environment maintaining apparatus 1 of this embodiment will be described below.

(Step S1)

Hydrogen peroxide gas is introduced into the working chamber 20 from the hydrogen peroxide introduction system 30. Specifically, the controller 2 controls the valve 32 to open so that hydrogen peroxide gas is introduced into the working chamber 20 from the hydrogen peroxide gas source 31 through the pipe 30A via the HEPA filter 26.

At this time, the controller 2 may control the valve 43 of the clean air introduction system 40 and the valve 61 of the exhaust system 60 to be closed. The valve 51 of the gas circulation system 50 may be either closed, or the valve 51 may be opened to allow the hydrogen peroxide to be circulated.

Sterilization of the interior of the working chamber 20 is executed by this step S1. This step S1 corresponds to step (a).

(Step S2)

The supply of the hydrogen peroxide gas is stopped, and clean air is introduced into the working chamber 20 from the clean air introduction system 40. Specifically, the controller 2 controls the valve 32 to close, and the valve 43 to open, so that clean air that flows through the pipe 40A and pipe 40B is introduced into the working chamber 20 via the HEPA filter 25.

The controller 2 then controls the valve 61 of the exhaust system 60 to open. This allows the clean air being supplied to push the hydrogen peroxide gas inside the working chamber 20 out of the exhaust system 60. Since the exhaust system 60 is provided with the catalyst 62 that decomposes hydrogen peroxide as described above, the gas exhausted out of the system contains a concentration of hydrogen peroxide reduced to or below the level specified by the safety standard. For the catalyst 62, rare metals such as palladium, rhodium, platinum and the like, or metal oxides such as manganese dioxide, iron (II) oxide, nickel oxide and the like may be used.

In performing this step S2, the valve 51 of the gas circulation system 50 may be remained open over a certain period of time to let the gas inside the working chamber 20 circulate to reduce the concentration of hydrogen peroxide, after which the valve 61 of the exhaust system 60 may be opened to exhaust the gas out of the system.

This step S2 corresponds to step (b), (Step S3)

The first ultraviolet light source 3 is illuminated. Thus the clean air present in the working chamber 20 is irradiated with ultraviolet having a peak wavelength of from 160 nm to less than 200 nm. As the ultraviolet is absorbed by the oxygen contained in the clean air, the reaction expressed by the following formula (1) occurs, and $O_2$ is decomposed into oxygen atoms, after which ozone ($O_3$) is generated by the reaction expressed by formula (2).

$$O_2 + h\nu(\lambda) \rightarrow O + O \quad (1)$$

$$O + O_2 \rightarrow O_3 \quad (2)$$

The ozone is introduced into the working chamber 20 by this step S3. This step S3 corresponds to step (c).

When executing this step S3, the valve 61 of the exhaust system 60 may be closed. This allows the ozone concentration in the working chamber 20 to be raised. It should be noted that the concentration of ozone in the working chamber 20 at this step S3 is expected to be 300 ppm or less at most, preferably about 10 to 80 ppm.

Step S3 may be carried out at the same time as the start of step S2.

(Step S4)

In the state in which the ozone is being introduced into the working chamber 20 by step S3, the visible light source 11 is illuminated. As mentioned above, the visible light source 11 is a light source capable of emitting visible light of a wavelength of 450 nm to 800 nm. This wavelength band has an overlap with the Chappuis band in the ozone absorption spectrum. Therefore, the visible light emitted from the visible light source 11 is absorbed by the ozone, and the ozone is decomposed as expressed by the following formula (3) as a result of the light energy given to the ozone, whereby oxygen radicals (·O) are obtained.

$$O_3 + h\nu(\lambda) \rightarrow O_2 + \cdot O \quad (3)$$

Part of the ozone introduced into the working chamber 20 by step S3 adheres to the surface of the placement unit 21 inside the working chamber 20. This ozone undergoes the reaction expressed by the above formula (3), so that oxygen radicals (·O) adhere to the surface of the placement unit 21. The oxygen radicals (·O) at this time react with the hydrogen peroxide remaining on the surface of the placement unit 21, and the reaction expressed by the following formula (4) occurs.

$$H_2O_2 + \cdot O \rightarrow \cdot HO_2 + \cdot OH \quad (4)$$

Since the hydroperoxyl radicals (·$HO_2$) and hydroxyl radicals (·OH) in the above formula (4) are highly reactive and short-lived, they instantly form more stable water ($H_2O$) or oxygen ($O_2$). Consequently, the hydrogen peroxide present on the surface of the placement unit 21 transforms into highly safe substances such as water and oxygen.

If the placement unit 21 is made of a resin material, the hydrogen peroxide introduced at step S1 may have penetrated into the placement unit 21. However, this step S4 causes highly reactive oxygen radicals (·O) to be generated, and the oxygen radicals (·O) decompose the hydrogen peroxide adhered to the surface of the placement unit 21, which creates a gradient in the concentration of hydrogen peroxide between the surface and the inside of the placement unit 21. This difference in concentration consequently causes the hydrogen peroxide that has penetrated into the placement unit 21 to vaporize and emerge on the surface of the placement unit 21 or outside thereof (i.e., in the space in the working chamber 20) to be more readily decomposed by the oxygen radicals (·O).

Ozone ($O_3$) is more reactive than oxygen ($O_2$), but less reactive than the oxygen radical (·O). Namely, a vast amount of ozone would be necessary to completely decompose hydrogen peroxide only with the ozone. This, however, would require a significant amount of catalyst 62 because of the need to remove the large amount of ozone by the catalyst 62 to allow for exhaust of the gas containing high-concentration ozone out of the system. Decomposition of hydrogen peroxide with ozone is expected to shorten the time necessary as compared to mere circulation of clean air to reduce the concentration of hydrogen peroxide in the working chamber 20. Even so, it would still take a very long time to decompose the hydrogen peroxide that has penetrated into the placement unit 21.

In contrast, according to the method of the present invention, the oxygen radical (·O), which is more reactive than ozone, is generated from ozone, and which reacts with hydrogen peroxide. Consequently, the hydrogen peroxide that has penetrated into the resin placement unit 21 can be decomposed in a short time.

This step S4 may be carried out until the concentration of the hydrogen peroxide in the working chamber 20 falls below a predetermined reference value. In this case, a sensor that measures the concentration of the hydrogen peroxide in the working chamber 20 may be provided, and the controller 2 may adjust the degree of opening of each valve (32, 43, 51, and 61) and control the illumination of the light sources (3 and 11) based on signals from this sensor.

This step S4 should preferably be executed in parallel with the supplying of ozone at step S3. This allows for generation of oxygen radicals (·O) at a high concentration.

The visible light source 11 should more preferably be configured to be able to emit visible light of a wavelength of 500 nm to 700 nm. The light source is not limited to a white LED that emits broad band spectrum light and may be a blue LED or a red LED that is capable of emitting a narrow band spectrum light.
(Step S5)

After the decomposition of hydrogen peroxide has progressed, the valve 43 of the clean air introduction system 40 and the valve 61 of the exhaust system 60 are opened so that the gas inside the working chamber 20 is discharged out of the system while the working chamber 20 is filled with clean air.

<<Other Configuration Examples>>

In the embodiment above, the ozone decomposition at step S4 is described as a step of irradiating ozone with visible light emitted from the visible light source 11. As long as the ozone is decomposed, step S4 may adopt various other methods.

Figure 2:
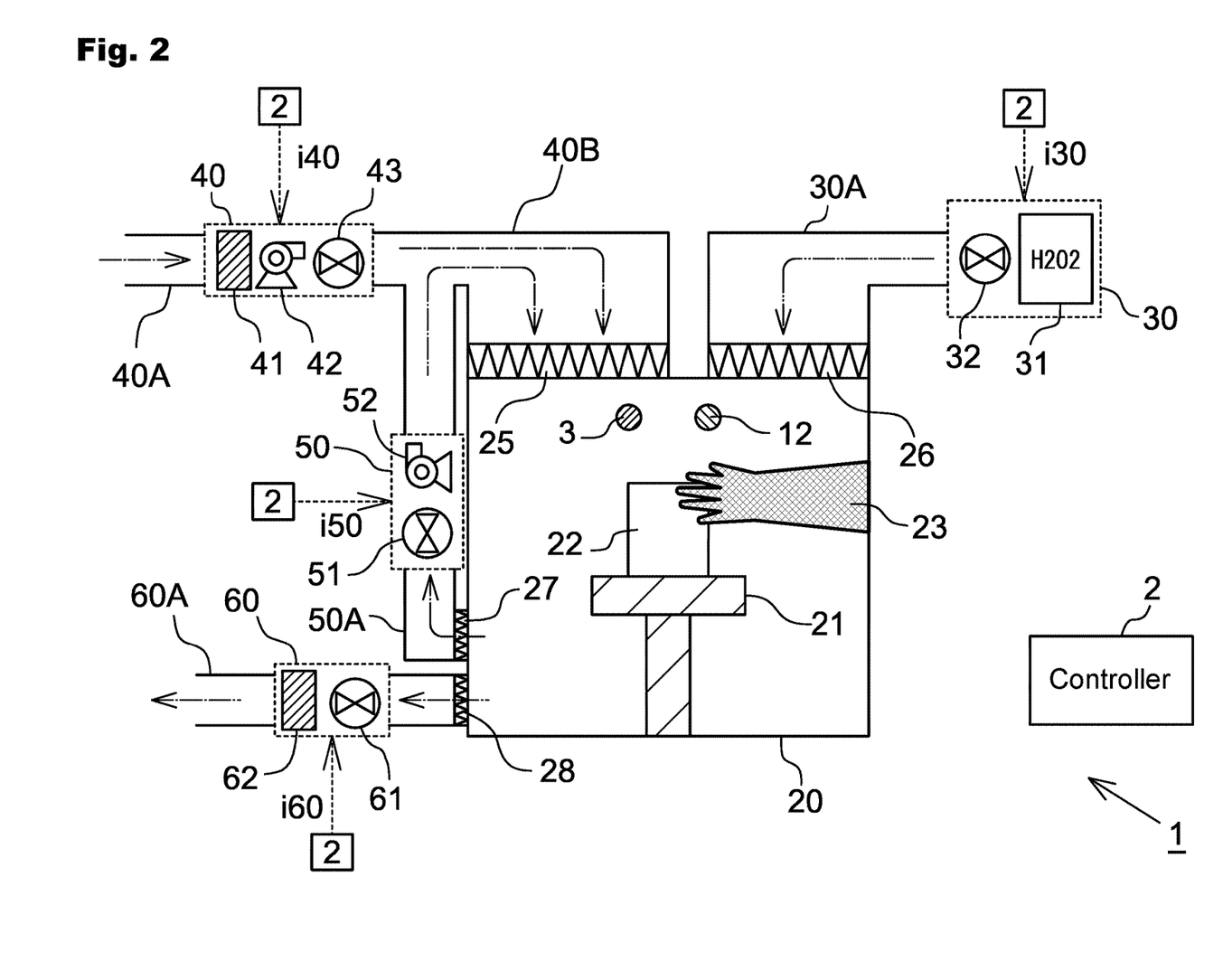
FIG. 2 is a drawing illustrating another schematic configuration of a sterile environment maintaining apparatus according to the first embodiment of the present invention.

<1> For example, as illustrated in FIG. 2, the sterile environment maintaining apparatus 1 may include an infrared light source 12 inside the working chamber 20. This infrared light source 12 is a light source capable of emitting infrared light of a wavelength of 1500 nm to 3000 nm, and may be an infrared LED or an infrared laser device, for example.

At step S4 described above, the infrared light source 12 is illuminated. The ozone irradiated with the infrared light is decomposed into oxygen radicals by the heat energy originating from the infrared light given to the ozone.

The infrared light of a wavelength of 1500 nm to 3000 nm is a wavelength band easily absorbed by water. Therefore, the infrared light emitted from the infrared light source 12 is absorbed by the water present on the surface as a result of the hydrogen peroxide having adhered on the surface of the placement unit 21 and been partly decomposed. As a result, the temperature of the surface or the inside of the placement unit 21 rises, which increases the diffusion rate of the hydrogen peroxide. This causes the hydrogen peroxide that has penetrated into the placement unit 21 to vaporize and to be exposed more readily on the surface, and this way the decomposition of hydrogen peroxide is accelerated.

Figure 3:
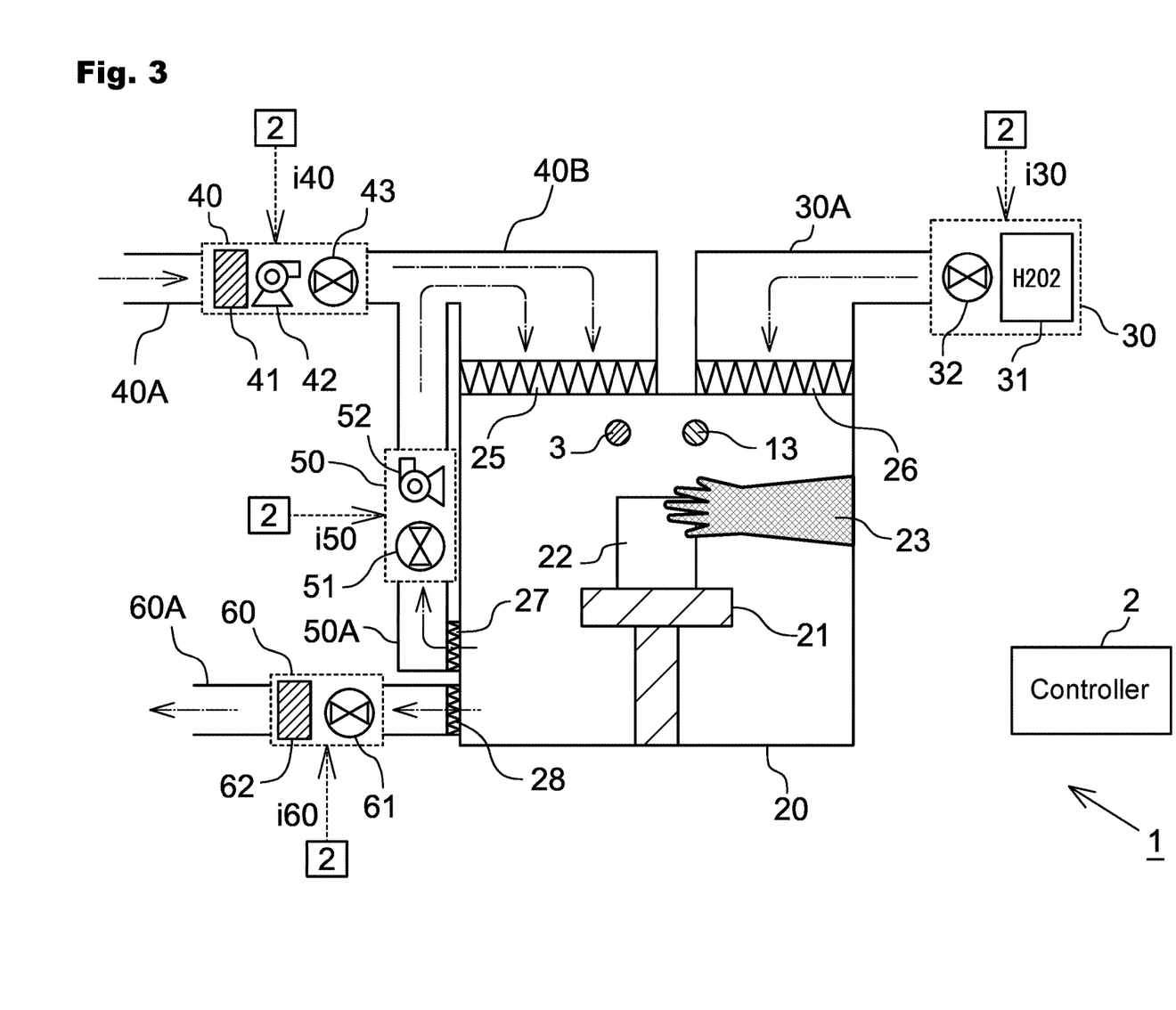
FIG. 3 is a drawing illustrating another schematic configuration of a sterile environment maintaining apparatus according to the first embodiment of the present invention.

<2> For example, as illustrated in FIG. 3, the sterile environment maintaining apparatus 1 may include a second ultraviolet light source 13 inside the working chamber 20. This second ultraviolet light source 13 is a light source capable of emitting ultraviolet of a wavelength of 190 nm to 320 nm, and may be an ultraviolet LED or an ultraviolet laser device, or an excimer lamp containing KrCl or XeCl as the light emitting gas, for example.

In this case, at step S4, the second ultraviolet light source 13 is illuminated based on a control signal from the controller 2. The ultraviolet wavelength band emitted from the second ultraviolet light source 13 has an overlap with the Hartley band or Huggins band in the ozone absorption spectrum. Therefore, the ultraviolet emitted from the second ultraviolet light source 13 is absorbed by the ozone, and the ozone is decomposed as expressed by the formula (3) above as a result of the light energy given to the ozone, whereby oxygen radicals (·O) are obtained.

Moreover, the ultraviolet of this wavelength band can also decompose the hydrogen peroxide itself by the following formula (5).

$$H_2O_2 + h\nu(\lambda) \rightarrow 2 \cdot HO \qquad (5)$$

Figure 4:
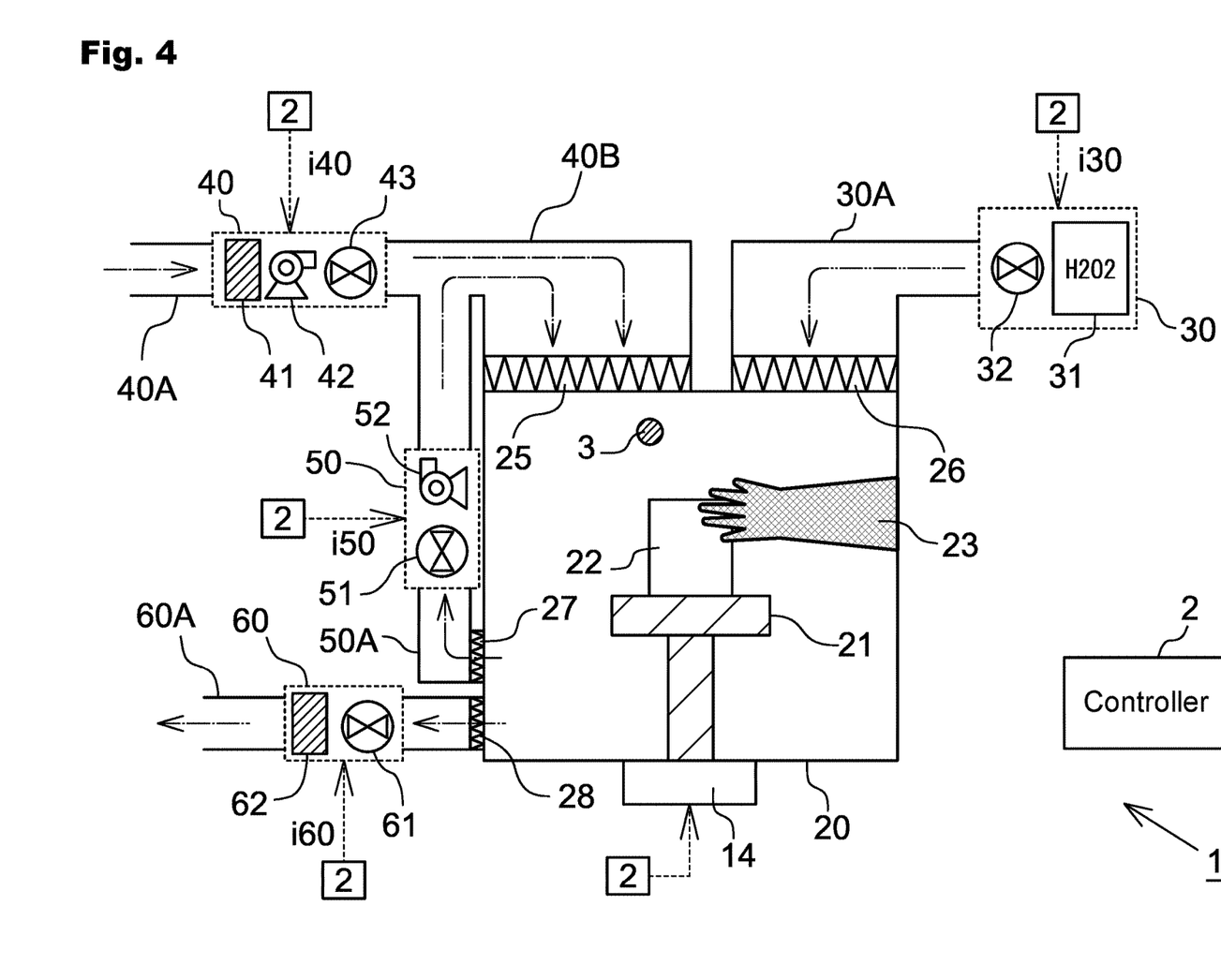
FIG. 4 is a drawing illustrating another schematic configuration of a sterile environment maintaining apparatus according to the first embodiment of the present invention.

<3> For example, as illustrated in FIG. 4, the sterile environment maintaining apparatus 1 may include a heater device 14 for raising the temperature inside the working chamber 20. In this case, at step S4, the heater device 14 is turned on based on a control signal from the controller 2 to raise the temperature inside the working chamber 20. Since the reactivity of the ozone increases as the surrounding temperature rises, the ozone is more easily decomposed by the formula (3) above so that oxygen radicals (·O) are more readily obtained.

In the case where the sterile environment maintaining apparatus 1 includes the heater device 14, it is preferable to turn on the heater device 14 after the working chamber 20 has been sufficiently filled with ozone by step S3. This prevents a large amount of ozone from being decomposed before the ozone adheres to the surface of the placement unit 21. To allow the temperature of the working chamber 20 to rise more easily, it is preferable to close the valve 61 of the exhaust system 60 when executing step S4.

Figure 5:
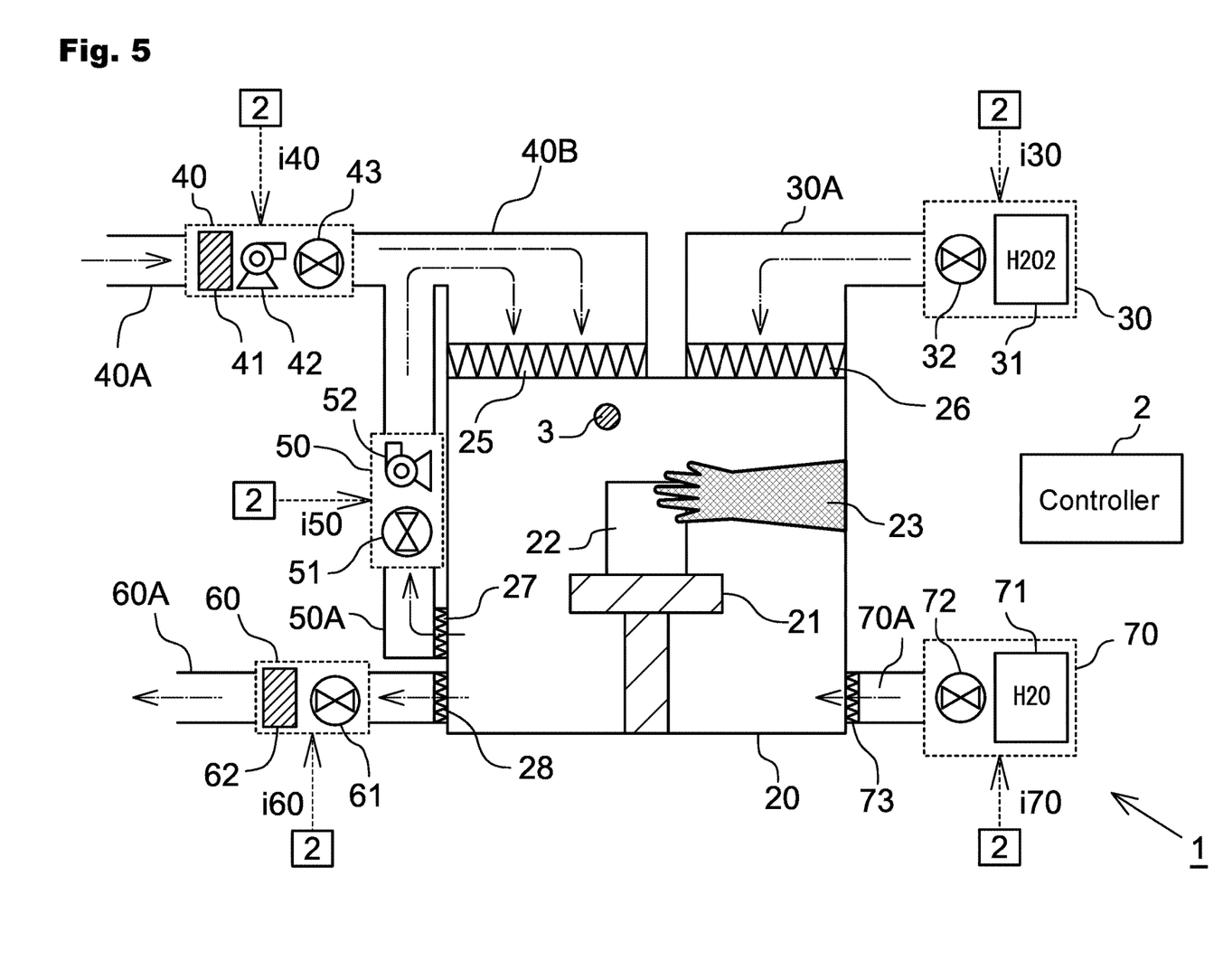
FIG. 5 is a drawing illustrating another schematic configuration of a sterile environment maintaining apparatus according to the first embodiment of the present invention.

<4> For example, as illustrated in FIG. 5, the sterile environment maintaining apparatus 1 may include a mist supply system 70 for raising the humidity inside the working chamber 20. The mist supply system 70 includes a mist generation device 71 and a valve 72, and is configured to be able to supply water mist delivered through the valve 72 into the working chamber 20 via a pipe 70A. The mist generation device 71 and valve 72 are controlled based on a control signal i70 from the controller 2. A HEPA filter 73 is disposed in the pipe 70A.

In this case, at step S4, the valve 72 is opened based on a control signal from the controller 2, and the water mist generated by the mist generation device 71 is introduced into the working chamber 20 to raise the humidity inside the working chamber 20. The ozone decomposition is accelerated as the reactivity increases with the rising surrounding humidity, making it easier to obtain oxygen radicals (·O).

<5> The visible light source 11 in FIG. 1, infrared light source 12 in FIG. 2, and second ultraviolet light source 13 in FIG. 3 may all be a flash light source capable of flash radiation. As this supplies instantaneous high energy to the ozone, oxygen radicals (·O) can be generated instantaneously at a high concentration. Consequently, an instantaneous increase in the difference in hydrogen peroxide concentration between the inside and the surface of the placement unit 21 enhances the effect of causing the hydrogen peroxide that has penetrated into the placement unit 21 to vaporize to the surface.

<6> The sterile environment maintaining apparatus 1 may include two or more of the visible light source 11, infrared light source 12, second ultraviolet light source 13, heater device 14, and mist supply system 70 described above.

Second Embodiment

Figure 6:
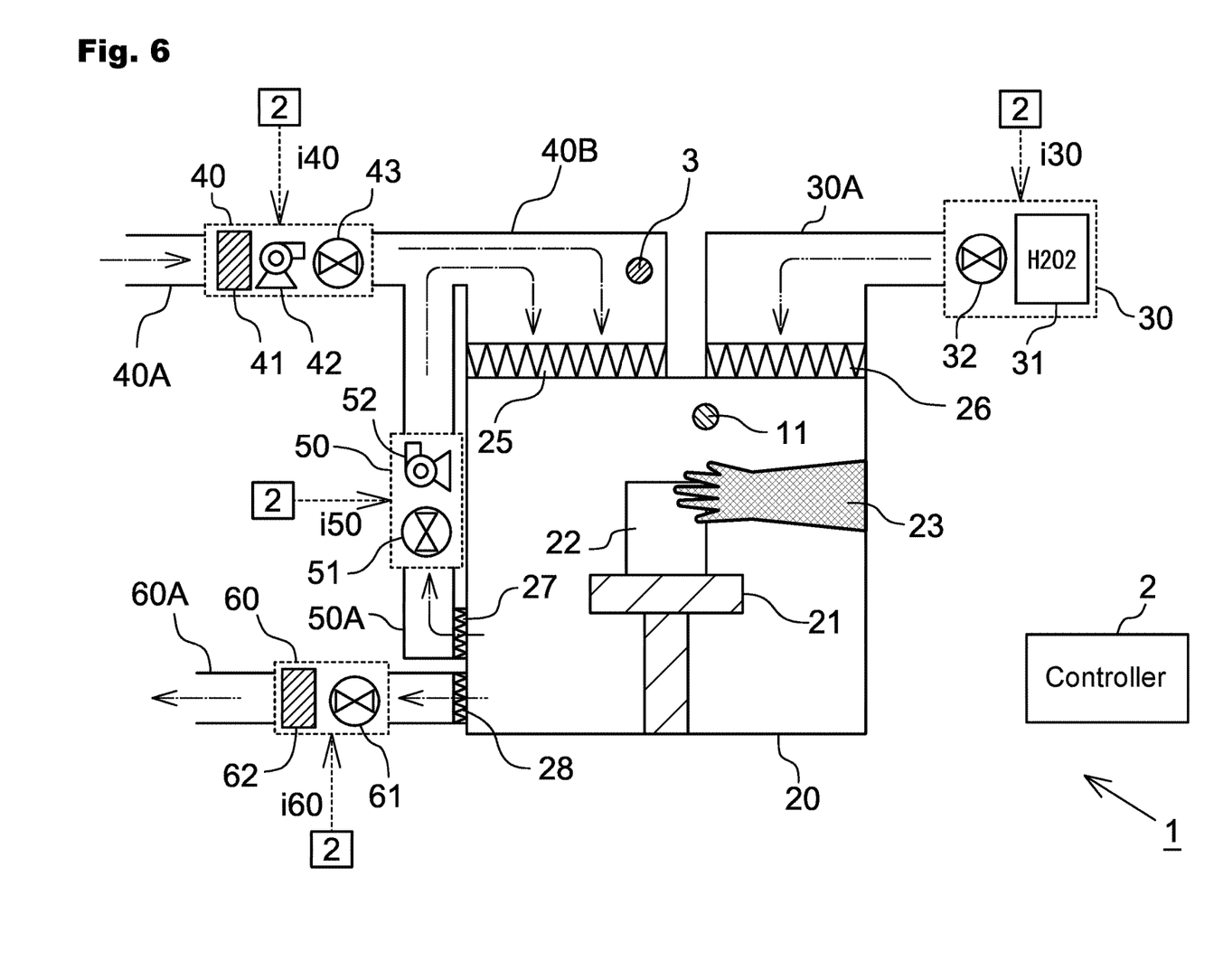
FIG. 6 is a drawing illustrating a schematic configuration of a sterile environment maintaining apparatus according to a second embodiment of the present invention.

A second embodiment of a sterile environment maintaining method and a sterile environment maintaining apparatus according to the present invention will be described, mainly centering on the points different from the first embodiment. FIG. 6 is a drawing illustrating a schematic configuration of the sterile environment maintaining apparatus according to the second embodiment of the present invention.

The sterile environment maintaining apparatus 1 illustrated in FIG. 6 is different in that the first ultraviolet light source 3 is not present inside the working chamber 20 but provided in the pipe 40B. In a case where the sterile environment maintaining apparatus 1 is utilized for pharmaceutical applications, it is expected that the first ultraviolet light source 3 that is an excimer lamp may not be allowed to be disposed inside the working chamber 20 as specified by the GMP (Good Manufacturing Practices) guidelines.

Even in such a case, by disposing the first ultraviolet light source 3 inside the pipe 40B upstream of the HEPA filter 25, the clean air can be irradiated with ultraviolet having a peak wavelength of from 160 nm to less than 200 nm at step S3. Ozone can thus be introduced into the working chamber 20.

Figure 7:
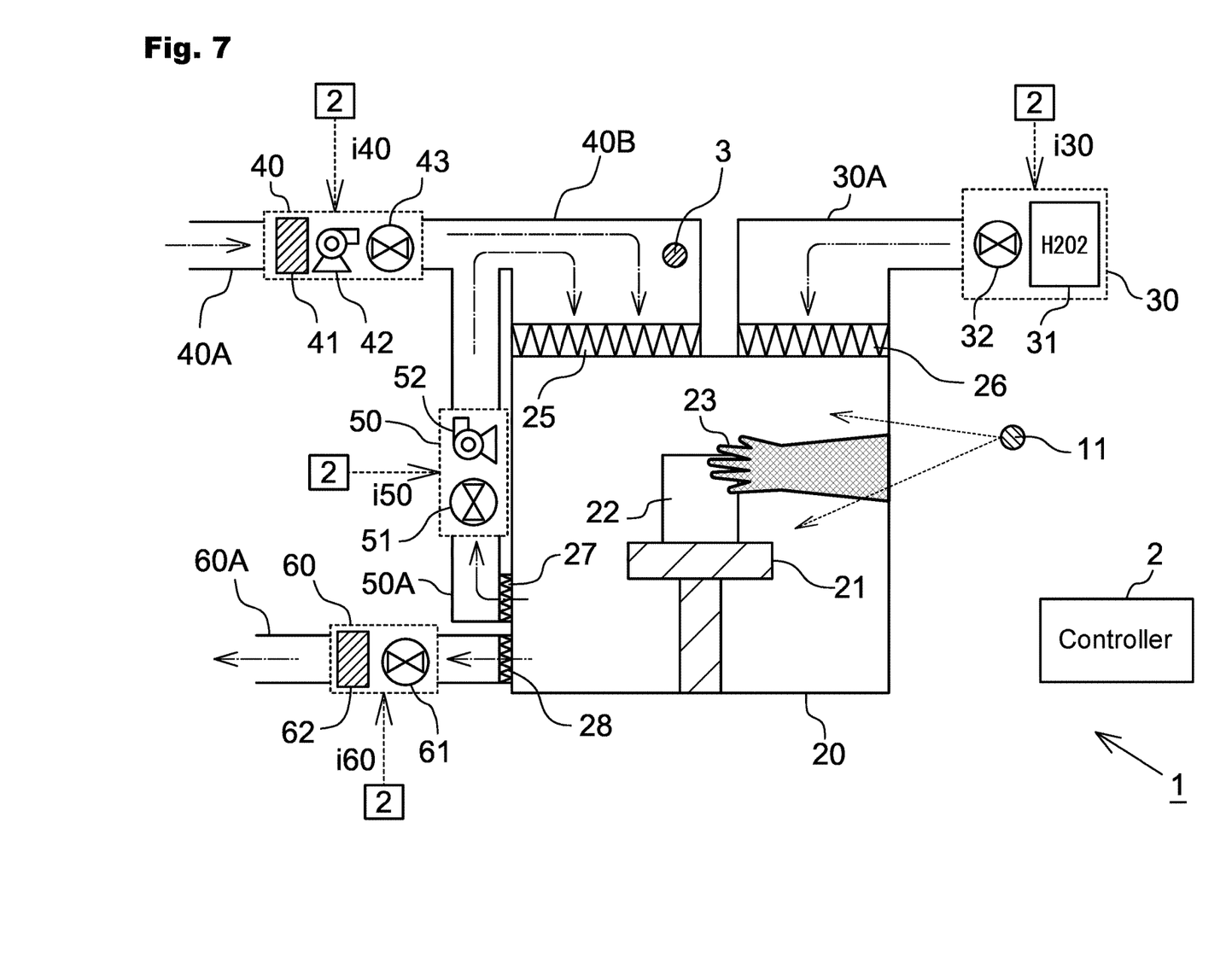
FIG. 7 is a drawing illustrating another schematic configuration of a sterile environment maintaining apparatus according to the second embodiment of the present invention.

Furthermore, in a case where even the visible light source 11 is not allowed to be provided inside the working chamber 20 because of restrictions imposed by the guidelines mentioned above or the like, visible light may be emitted from a visible light source 11 disposed outside the working chamber 20 into the working chamber 20 as illustrated in FIG. 7 through a window part (not shown) that forms part of the wall surface of the working chamber 20. In the case where the second ultraviolet light source 13 is disposed outside the working chamber 20, it is necessary to form the window part mentioned above with a material that can transmit the ultraviolet emitted from the second ultraviolet light source 13.

In this embodiment, any of the visible light source 11, infrared light source 12, and second ultraviolet light source 13 may be disposed outside the working chamber 20, and the light may be introduced into the working chamber 20 via a light guide member such as an optical fiber.

Third Embodiment

Figure 8:
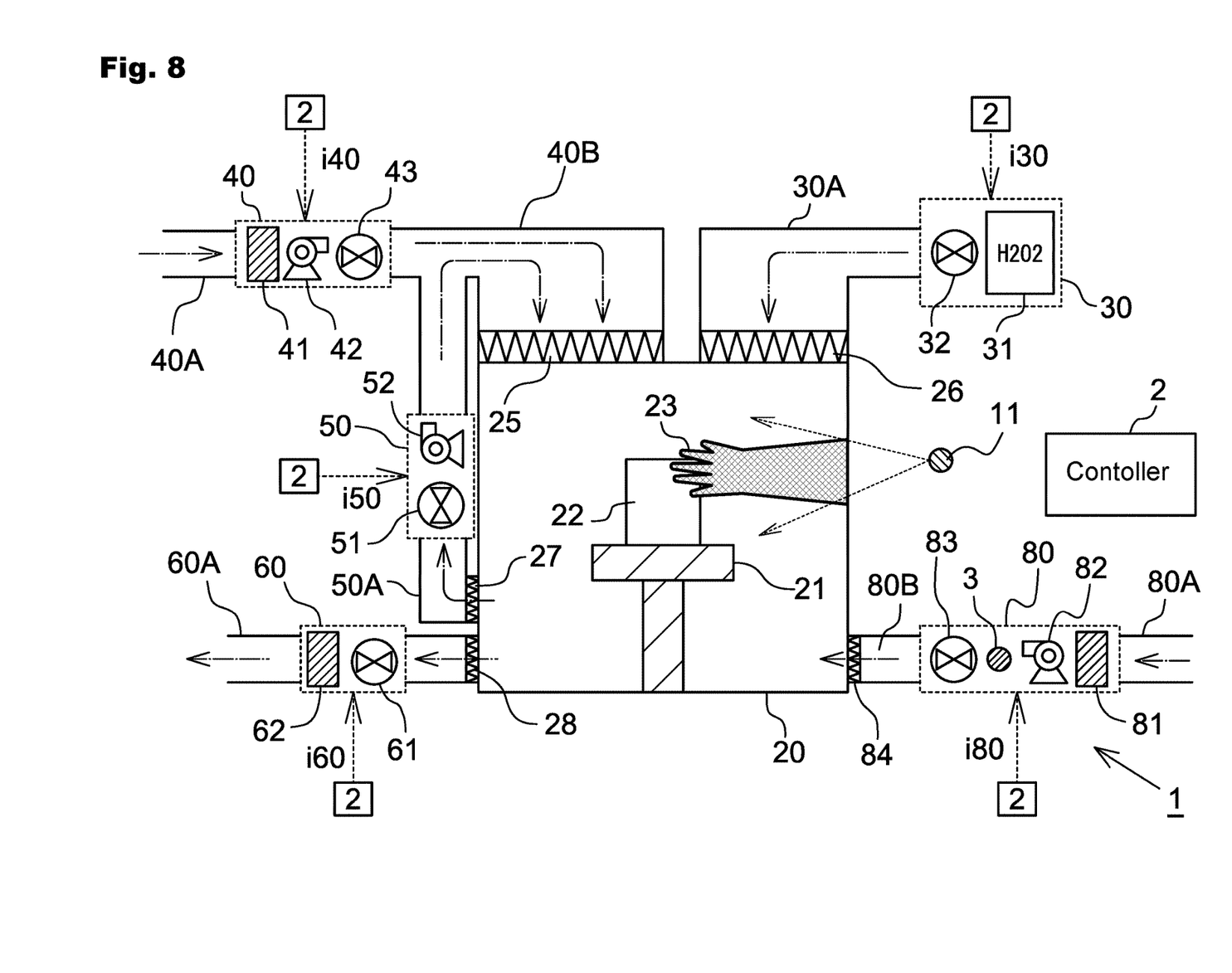
FIG. 8 is a drawing illustrating a schematic configuration of a sterile environment maintaining apparatus according to a third embodiment of the present invention.

A third embodiment of a sterile environment maintaining method and a sterile environment maintaining apparatus according to the present invention will be described, mainly centering on the points different from the first embodiment and the second embodiment. FIG. 8 is a drawing illustrating a schematic configuration of the sterile environment maintaining apparatus according to the third embodiment of the present invention.

In a case where the sterile environment maintaining apparatus 1 is utilized for pharmaceutical applications, it is expected that the first ultraviolet light source 3 that is an excimer lamp may not be allowed to be disposed, let alone inside the working chamber 20, but even inside the pipe 40B through which clean air is introduced, as specified by the GMP guidelines. In view of such a circumstance, the sterile environment maintaining apparatus 1 illustrated in FIG. 8 has an ozone introduction system 80 including the first ultraviolet light source 3 in an isolated location separate from the pipe 40B through which clean air is introduced.

More particularly, the ozone introduction system 80 includes a catalyst 81, a blower 82, a valve 83, and the first ultraviolet light source 3. The blower 82, valve 83, and first ultraviolet light source 3 are controlled based on a control signal i80 from the controller 2. The ozone introduction system 80 generates ozone by irradiating the clean air supplied from a pipe 80A with ultraviolet having a peak wavelength of from 160 nm to less than 200 nm from the first ultraviolet light source 3. The air containing the ozone is introduced into the working chamber 20 from a pipe 80B via a HEPA filter 84.

The sterile environment maintaining apparatus 1 illustrated in FIG. 8, similarly to FIG. 7, is also configured to be capable of emitting visible light from a visible light source 11 disposed outside the working chamber 20 into the working chamber 20 through a window part (not shown) that forms part of the wall surface of the working chamber 20.

With this configuration, after the clean air is introduced into the working chamber 20 from the clean air introduction system 40 at step S2, ozone is introduced into the working chamber 20 from the ozone introduction system 80 at step S3. After that, at step S4, the ozone inside the working chamber 10 is irradiated with the visible light emitted from the visible light source 11 from outside the working chamber 10. This causes part of the ozone to be decomposed into oxygen radicals (·O).

In this embodiment, when introducing the air containing the ozone at step S3, the valve 43 of the clean air introduction system 40 may be controlled to close.

Similarly to the second embodiment, the sterile environment maintaining apparatus 1 of this embodiment may include an infrared light source 12 or a second ultraviolet light source 13 disposed outside the working chamber 20 instead of the visible light source 11, or include a heater device 14 or a mist supply system 70.

Other Embodiments

Other embodiments are described below.

<1> The sterile environment maintaining apparatus 1 in each embodiment described above is illustrated as having the pipe 30A for introducing hydrogen peroxide into the working chamber 20 and the pipe 40B for introducing clean air into the working chamber 20 separate from each other. In a case where the degree of opening of each valve (32, 43, and 51) can be adjusted highly precisely, one pipe can serve as both pipe 30A and pipe 40B. In this case, one filter alone can serve as HEPA filter 25 and HEPA filter 26.

Figure 9:
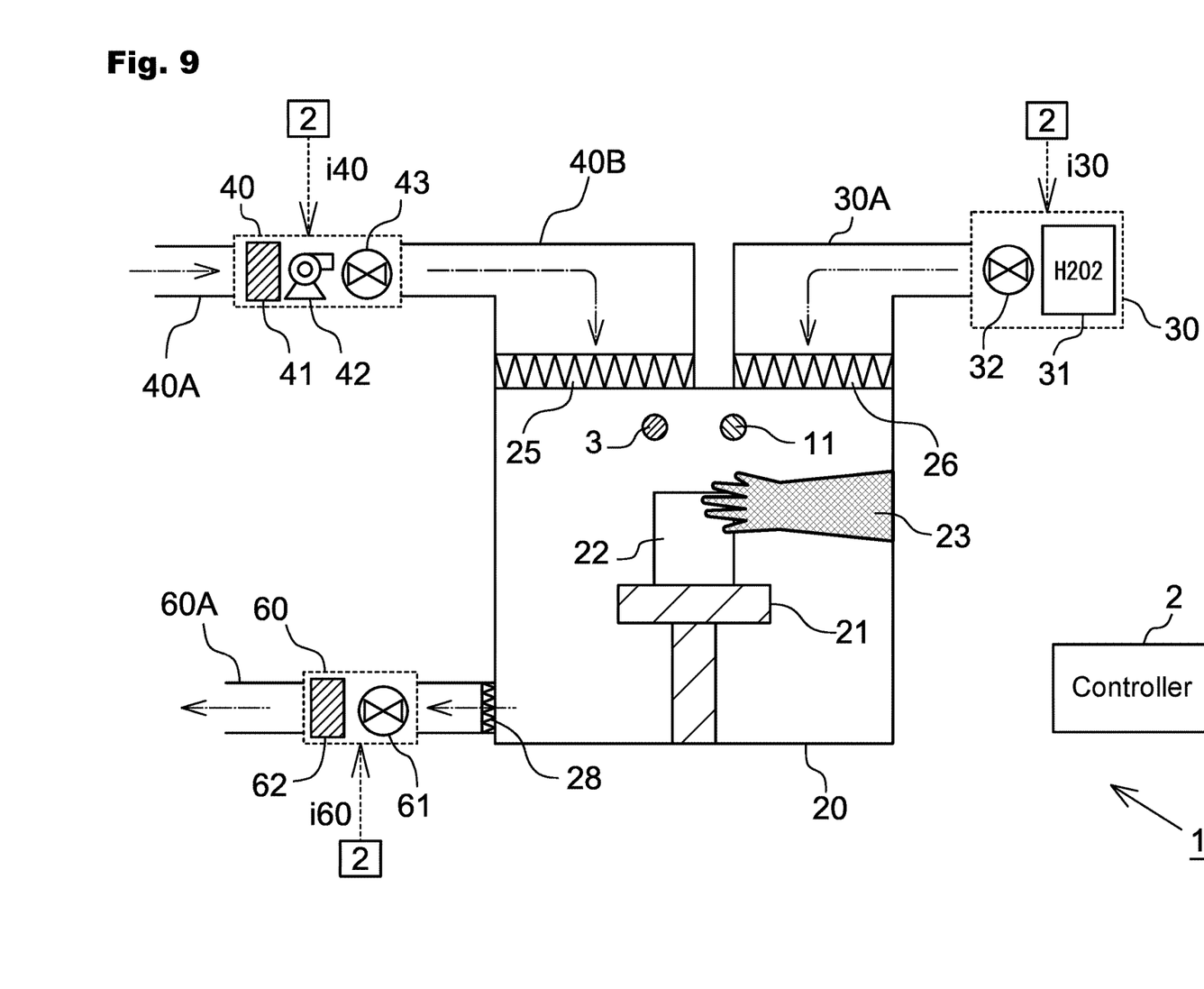
FIG. 9 is a drawing illustrating a schematic configuration of a sterile environment maintaining apparatus according to another embodiment of the present invention.

<2> While the sterile environment maintaining apparatus 1 of each embodiment described above includes the gas circulation system 50 for circulating the gas inside the working chamber 20 through the pipe 50A, the apparatus may not include the pipe 50A and the gas circulation system 50 as illustrated in FIG. 9.

<3> The sterile environment maintaining apparatus 1 is applicable also to clean benches and chambers and not just isolators.

What is claimed is:

1. A method of maintaining a sterile environment of a working chamber that contains a resin component, comprising:
    a step (a) of introducing hydrogen peroxide into the working chamber;
    a step (b) of introducing clean air for aeration into the working chamber through a filter to push out the hydrogen peroxide inside the working chamber to an exhaust system after completion of the step (a);
    a step (c) of generating ozone by irradiating the clean air with ultraviolet having a peak wavelength of from 160 nm to less than 200 nm upstream of the filter or inside the working chamber and introducing the ozone into the working chamber;
    a step (d) of decomposing the ozone introduced into the working chamber into oxygen radicals; and
    a step (e) of decomposing the hydrogen peroxide remaining adhered to the resin component by the oxygen radicals,
    wherein the step (d) includes a step (d1) of emitting visible light of a wavelength of 450 nm to 800 nm into the working chamber (20).

2. A method of maintaining a sterile environment of a working chamber that contains a resin component, comprising:
    a step (a) of introducing hydrogen peroxide into the working chamber;
    a step (b) of introducing clean air for aeration into the working chamber through a filter to push out the hydrogen peroxide inside the working chamber to an exhaust system after completion of the step (a);

a step (c) of generating ozone by irradiating the clean air with ultraviolet having a peak wavelength of from 160 nm to less than 200 nm upstream of the filter or inside the working chamber and introducing the ozone into the working chamber;

a step (d) of decomposing the ozone introduced into the working chamber into oxygen radicals; and a step (e) of decomposing the hydrogen peroxide remaining adhered to the resin component by the oxygen radicals, wherein the step (d) includes a step (d2) of emitting infrared light of a wavelength of 1500 nm to 3000 nm into the working chamber (20).

3. A method of maintaining a sterile environment of a working chamber that contains a resin component, comprising:

a step (a) of introducing hydrogen peroxide into the working chamber;

a step (b) of introducing clean air for aeration into the working chamber through a filter to push out the hydrogen peroxide inside the working chamber to an exhaust system after completion of the step (a);

a step (c) of generating ozone by irradiating the clean air with ultraviolet having a peak wavelength of from 160 nm to less than 200 nm upstream of the filter or inside the working chamber and introducing the ozone into the working chamber;

a step (d) of decomposing the ozone introduced into the working chamber into oxygen radicals; and a step (e) of decomposing the hydrogen peroxide remaining adhered to the resin component by the oxygen radicals, wherein the step (d) includes a step (d3) of emitting ultraviolet of a wavelength of 190 nm to 320 nm from an ultraviolet light source disposed inside the working chamber (20).

4. The method of maintaining a sterile environment of a working chamber according to claim 1, wherein the step (c) is started later than the start of the step (b).

5. The method of maintaining a sterile environment of a working chamber according to claim 2, wherein the step (c) is started later than the start of the step (b).

6. The method of maintaining a sterile environment of a working chamber according to claim 3, wherein the step (c) is started later than the start of the step (b).

7. The method of maintaining a sterile environment of a working chamber according to claim 4, wherein the step (c) includes a time period in which introduction of the air into the working chamber is stopped.

8. The method of maintaining a sterile environment of a working chamber according to claim 5, wherein the step (c) includes a time period in which introduction of the air into the working chamber is stopped.

9. The method of maintaining a sterile environment of a working chamber according to claim 6, wherein the step (c) includes a time period in which introduction of the air into the working chamber is stopped.

\* \* \* \* \*